(12) United States Patent
Murray et al.

(10) Patent No.: US 9,765,375 B2
(45) Date of Patent: Sep. 19, 2017

(54) METHODS FOR DEVELOPING BINDING-ELEMENTS AND USES THEREOF

(71) Applicant: General Electric Company, Schenectady, NY (US)

(72) Inventors: Anthony John Murray, Lebanon, NJ (US); John Richard Nelson, Clifton Park, NY (US)

(73) Assignee: General Electric Company, Niskayuna, NY (US)

( * ) Notice: Subject to any disclaimer, the term of this patent is extended or adjusted under 35 U.S.C. 154(b) by 218 days.

(21) Appl. No.: 13/929,976

(22) Filed: Jun. 28, 2013

(65) Prior Publication Data

US 2015/0004611 A1 Jan. 1, 2015

(51) Int. Cl.
| | | |
|---|---|---|
| *C12P 19/34* | (2006.01) |
| *C12Q 1/68* | (2006.01) |
| *C12N 15/115* | (2010.01) |
| *C12N 15/11* | (2006.01) |

(52) U.S. Cl.
CPC ............ *C12P 19/34* (2013.01); *C12N 15/111* (2013.01); *C12N 15/115* (2013.01); *C12N 2310/16* (2013.01); *C12N 2320/10* (2013.01)

(58) Field of Classification Search
None
See application file for complete search history.

(56) References Cited

U.S. PATENT DOCUMENTS

| | | | |
|---|---|---|---|
| 6,207,388 B1 | 3/2001 | Grossman | |
| 6,458,559 B1 | 10/2002 | Shi et al. | |
| 2002/0064779 A1* | 5/2002 | Landegren et al. | 435/6 |
| 2004/0219520 A1 | 11/2004 | Mirkin et al. | |
| 2005/0069938 A1* | 3/2005 | Wang et al. | 435/6 |
| 2006/0166222 A1 | 7/2006 | Lu et al. | |
| 2008/0293051 A1 | 11/2008 | Levy et al. | |
| 2009/0061424 A1 | 3/2009 | Chen | |
| 2009/0209430 A1 | 8/2009 | Rasmussen | |
| 2010/0152056 A1* | 6/2010 | Lopreato | 506/9 |
| 2010/0240544 A1 | 9/2010 | Liu et al. | |
| 2011/0136099 A1* | 6/2011 | Schneider et al. | 435/5 |
| 2011/0263459 A1 | 10/2011 | Borer et al. | |
| 2013/0164739 A1 | 6/2013 | Heemstra | |

FOREIGN PATENT DOCUMENTS

| | | |
|---|---|---|
| WO | 9214843 A1 | 9/1992 |
| WO | 02/10186 A1 | 2/2002 |
| WO | 2004083427 A2 | 9/2004 |
| WO | 2007/027796 A2 | 3/2007 |
| WO | 2007117444 A2 | 10/2007 |
| WO | 2007128004 A2 | 11/2007 |
| WO | 2009021031 A2 | 2/2009 |
| WO | 2011/059453 A1 | 5/2011 |

OTHER PUBLICATIONS

Hoon et al. Aptamer selection by high-throughput sequencing and informatic analysis. BioTechniques (2011) vol. 51, No. 6, pp. 413-416.*

Lalonde et al. Sensitive oligonucleotide ligation assay for low-level detection of nevirapine resistance mutations in human immunodeficiency virus type 1 quasispecies. J. Clinical Microbiology (2007) vol. 45, No. 8, pp. 2604-2615.*

Matthew Levy et al: "Peptide-Templated Nucleic Acid Ligation", Journal of Molecular Evolution., vol. 56, No. 5, May 2003, pp. 607-615, XP55333864, US, ISSN: 0022-2844, DOI:1007/s00239-002-2429-7s00239-002-2429-7.

Di Giusto D A et al: "Construction, stability, and activity of multivalent circular anticoagulant aptamers", Journal of Biological Chemistry, American Society for Biochemistry and Molecular Biology, US, vol. 279, No. 45, Nov. 5, 2004, pp. 46483-46489, XP002600154, ISSN: 0021-9258, DOI:10.1074/JBC.M408037200 [retrieved on Aug. 18, 2004] *figures 1, 2, 5.

Kwame Sefah et al: "Nucleic acid aptamers for biosensors and bio-analytical applications", The Analyst, vol. 134, No. 9, Jun. 23, 2009, p. 1765, XP55081133, ISSN: 0003-2654. DOI: 10.1039/b905609m *figure 3*.

Yi-Tak Lai et al: "A primer-free method that selects high-affinity single-stranded DNA aptamers using thermostable RNA ligase", Analytical Biochemistry, Elsevier, Amsterdam, NL, vol. 414, No. 2, Mar. 21, 2011, pp. 246-253, XP028210315, ISSN: 0003-2697, DOI: 10.1016/J.AB.2011.03.018 [retrieved on Mar. 21, 2011] *figure 1*.

Daniel A. Di Giusto et al: "Multitasking by Multivalent Circular DNA Aptamers", Chembiochem—A European Journal of a Chemical Biology., vol. 7, No. 3, Feb. 15, 2006, pp. 535-544, XP055334470, DE ISSN: 1439-4227, DOI: 10.1002/cbic.200500316 *the whole document*.

R. E. Wang et al: "Improving the Stability of Aptamers by Chemical Modification", Current Medicinal Chemistry, vol. 18, No. 27, Sep. 2011, pp. 4126-4138, XP055216480, ISSN: 0929-8673, DOI: 10.2174/092986711797189565 * figure1 *.

C. Frauendorf: "Internal 32P-labeling of L-deoxyoligonucleotides", Nucleic Acids Research, vol. 31, No. 7, Apr. 2003, pp. 34e-34, XP55334943, DOI: 10.1093/nar/gng034 "The whole document".

Orada Chumphukam: "Proximity dependent ligation selection: a new approach to generating dna aptamers", Sep. 2013, XP55333836, Retrieved from the Internet: URL:https://spiral, imperial . ac . uk:8443/bitstream/10044/1/24836/1/Chumphukam-0/2014-P hD-Thesis.pdf [retrieved on Jan. 10, 2017] * p. 84-p. 86; figure 2.6 *.

Extended European Search Report mailed Jan. 23, 2017 in counterpart European Application No. 14816644.0-1401/ 3013982 PCT/SE2014050775.

(Continued)

*Primary Examiner* — David Thomas

(74) *Attorney, Agent, or Firm* — Pabitra K. Chakrabarti

(57) ABSTRACT

Methods for developing a binding-element are provided. A mixture comprising a target molecule, a plurality of oligonucleotides and a ligase is provided, followed by binding the oligonucleotides to the target molecule to form an oligonucleotides-target molecule complex. The oligonucleotides bound to the target molecule are ligated to form the binding-element. The binding-elements are separated from the mixture.

25 Claims, 2 Drawing Sheets

(56) References Cited

OTHER PUBLICATIONS

Schutze, T. et al. "Probing the SELEX Process with the Next-Generation Sequencing", In: PLOS One, Dec. 2011, vol. 6, Issue 12, pp. 1-10.
Fredriksson, S, et al. "Protein detection using proximity-dependent DNA ligation assays", in: Nature Biotech., May 2002, vol. 20, pp. 473-477.
PCT Search Report and Written Opinion issued in connection with corresponding PCT Application No. PCT/SE2014/050775 on Oct. 20, 2014.
Yamamoto-Fujita et al., "Aptamer-Derived Nucleic Acid Oligos: Applications to Develop Nucleic Acid Chips to Analyze Proteins and Small Ligands", Analytical Chemistry, pp. 5460-5466, vol. 77, issue 17, Jul. 29, 2005.
Sharma et al., "Small-Molecule-Dependent Split Aptamer Ligation", Journal of American Chemical Society, pp. 12426-12429, vol. 133, issue 32, Jul. 16, 2011.

\* cited by examiner

METHODS FOR DEVELOPING BINDING-ELEMENTS AND USES THEREOF

FIELD OF INVENTION

The invention generally relates to methods for making binding-elements. The methods specifically relate to methods for making nucleic acid binding-elements to provide specific target binding.

BACKGROUND

Development of a binding element, such as a receptor, ligand or an aptamer, in relatively short span of time remains a key challenge with regard to fine tuning of selectivity, sensitivity and specificity of the binding elements. Antibodies are valued for their high selectivity and affinity, however, the size and complex structure of antibodies may cause the molecules to be susceptible to degradation, aggregation, modification or denaturation. In addition, therapeutic application requires antibodies produced in mammalian cell lines; which is an expensive and complex process.

Engineered protein binders based on stable protein scaffolds have proved to be a successful strategy for production of affinity ligands since these ligands are smaller than antibodies, and are relatively stable and can be synthesized in microbial production systems. While many of these binders might be unsuitable for therapeutic applications because of their potential immunogenicity, they have found application as binders in analytical, diagnostics and chromatographic applications.

Binding-elements, such as aptamers are oligonucleotide affinity ligands that are selected for their high affinity binding to molecular targets. A variety of binding-elements have been developed based on nucleic acid, such as DNA and RNA. Binding-element discovery to date involves a selection process from a large library of DNA, RNA or modified nucleic acid oligomers involving multiple selection processes, such as SELEX (systematic evolution of ligands by exponential enrichment). Many rounds of selection and amplification are usually required to discover binding-elements with the desired affinity and selectivity. Thus the currently known process for selecting binding-elements are labor-intensive, time-consuming and expensive.

Therefore, there is a need to develop an alternative approach for discovery of binding-elements that provide adequate target affinity with increased specificity, while screening against molecules having structure similar to the target molecules.

BRIEF DESCRIPTION

One or more embodiments of the methods for synthesizing a binding-element comprise providing a mixture comprising a plurality of target molecules, a plurality of oligonucleotides and a ligase, forming an oligonucleotides-target molecule complex, wherein two or more of the oligonucleotides are bound to at least one of the target molecules; ligating the oligonucleotides bound to the target molecules to form the binding-element, and separating the binding-element, wherein the binding element is configured to efficiently bind a target molecule through one or more binding sites.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
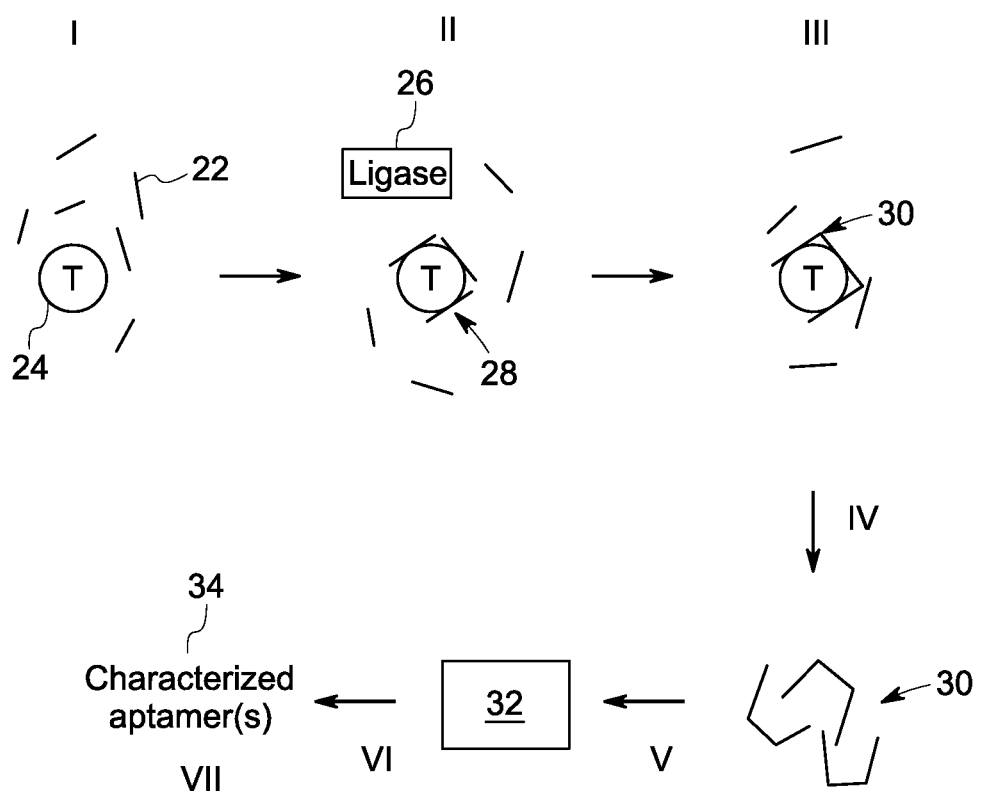
FIG. 1 is a schematic drawing showing method of synthesizing, selecting and purifying the binding-elements for specific target molecules in accordance with one embodiment of the invention.

The methods for synthesizing and selecting oligonucleotide-based binding-elements using the target molecule as a template are provided. The synthesized binding-elements have higher specificity and selectivity for the target molecules. The synthesis and selection methods are reliable and suitable for applications such as affinity purification of target molecules from a population of molecules having structure similar to the target.

To more clearly and concisely describe and point out the subject matter of the claimed invention, the following definitions are provided for specific terms, which are used in the following description and the appended claims. Throughout the specification, exemplification of specific terms should be considered as non-limiting examples.

The singular forms "a", "an" and "the" include plural referents unless the context clearly dictates otherwise. Approximating language, as used herein throughout the specification and claims, may be applied to modify any quantitative representation that could permissibly vary without resulting in a change in the basic function to which it is related. Accordingly, a value modified by a term such as "about" is not to be limited to the precise value specified. In some instances, the approximating language may correspond to the precision of an instrument for measuring the value. Similarly, "free" may be used in combination with a term, and may include an insubstantial number, or trace amounts while still being considered free of the modified term. Where necessary, ranges have been supplied, and those ranges are inclusive of all sub-ranges there between.

As used herein the term "nucleotide" or "nucleotide base" refers to a nucleoside phosphate. The term includes, but is not limited to, a natural nucleotide, a synthetic nucleotide, a modified nucleotide, or a surrogate replacement moiety (e.g., inosine). The nucleoside phosphate may be a nucleoside monophosphate, a nucleoside diphosphate or a nucleoside triphosphate. The sugar moiety in the nucleoside phosphate may be a pentose sugar, such as ribose, and the phosphate esterification site may correspond to the hydroxyl group attached to the C-5 position of the pentose sugar of the nucleoside. A nucleotide may be, but is not limited to, a deoxyribonucleotide triphosphate (dNTP) or a ribonucleotide triphosphate (NTP). The nucleotides may be represented using alphabetical letters, for example, A denotes adenosine (e.g., a nucleotide containing the nucleobase, adenine), C denotes cytosine, G denotes guanosine, and T denotes thymidine.

As used herein, the term "oligonucleotide" refers to oligomers of nucleotides or derivatives thereof. The term "nucleic acid" as used herein refers to polymers of nucleotides or derivatives thereof. The term "sequence" as used herein refers to a nucleotide sequence of an oligonucleotide or a nucleic acid. Throughout the specification, whenever an oligonucleotide/nucleic acid is represented by a sequence of letters, the nucleotides are in 5'→3' order from left to right.

The oligonucleotides/nucleic acids may be a DNA, an RNA, or their analogues (e.g., phosphorothioate analogue). The oligonucleotides or nucleic acids may also include modified bases and/or backbones (e.g., modified phosphate linkage or modified sugar moiety). Non-limiting examples of synthetic backbones that confer stability and/or other advantages to the nucleic acids may include phosphorothioate linkages, peptide nucleic acid, locked nucleic acid, xylose nucleic acid, or analogues thereof. The oligonucleotide refers to a short linear oligonucleotide that may include 5 to 30 nucleotides. The oligonucleotides may also interchangeably used herein as "oligomers" or "short oligomers". The oligonucleotide may be an RNA sequence, a DNA sequence, or a chimeric sequence. The oligonucleotide may contain natural, synthetic, or modified nucleotides. Both the upper and lower limits of the length of the oligonucleotide are empirically determined. The lower limit on oligonucleotide length is the minimum length that is required to form a transient complex upon binding with the target molecule under desired reaction conditions. Very short oligonucleotides (usually less than 3-4 nucleotides long) do not form thermodynamically stable complex with target molecule under such conditions. Generally, suitable oligonucleotide lengths are in the range of about 4 to about 30 nucleotides long.

As used herein, the terms "amplification", "nucleic acid amplification", or "amplifying" refer to the production of multiple copies of a nucleic acid template, or the production of multiple nucleic acid sequence copies that are complementary to the nucleic acid template, for example, a ligated oligonucleotide.

As used herein, the term "target molecule" refers to a molecule that is desired to be bound to one or more short oligomers present in the reaction mixture. For example, the target molecule may comprise a protein, a post-translationally modified protein, a peptide, a carbohydrate or a synthetic peptide. The target molecule is the molecule of interest, which either needs to be separated and purified out from a mixture of molecules or needs to be quantified or characterized. In one or more embodiments, the target molecules are also represented as templates.

As used herein the term "reaction mixture" or "mixture" refers to the combination of reagents or reagent solutions, which are used to carry out a chemical analysis or a biological assay. The reaction mixture or mixture may include oligomers, target molecules, ligase, buffer reagents, chelating agents or water.

One or more embodiments of the invention are directed to methods for synthesis and selection of nucleic acid binding-elements for affinity binding assays. The term "binding element" refers to herein as an oligonucleotide-based component that efficiently binds to a target molecule through one or more binding sites. The binding element may include an aptamer. In one or more embodiments, the binding element is nucleic acid aptamer, such as DNA aptamer or RNA aptamer.

In some embodiments, the methods for synthesizing a binding-element comprise providing a mixture comprising a plurality of target molecules, a plurality of oligonucleotides and a ligase. The methods further comprise forming an oligonucleotides-target molecule complex, wherein the oligonucleotides are bound to each of the target molecules, ligating the oligonucleotides bound to each of the target molecules to form the binding-element(s) and separating the binding-element(s). The term "oligonucleotides" or "oligomers" are used interchangeably, hereinafter.

As noted, the methods comprise providing a mixture comprising target molecules, a plurality of oligonucleotides and a ligase, wherein the target molecules, oligomers or ligase are added sequentially or simultaneously. In some embodiments, the oligomers and the target molecules are added simultaneously for synthesizing the binding-element. In this embodiment, the ligase is added separately after mixing the oligomers and the target molecules. In one or more embodiments, the target molecules, oligomers or ligase are mixed using different mixing techniques, such as by pipetting up and down, vortexing, mild shaking, waving or stirring.

The target molecule may be an organic molecule, an inorganic molecule, a synthetic molecule or combinations thereof. In one or more embodiments, the target molecule may be a protein, a post-translationally modified protein, a peptide, a carbohydrate, a drug, a carrier, a small molecule, an adapter or combinations thereof. The term "carrier" refers to a compound that may attach to one or more drug, protein, peptide, carbohydrate, lipid, genetic material or small molecule for targeted delivery and controlled release. The carrier may include a synthetic compound or a natural compound isolated from different sources. The carrier may be a nanoparticle. In one embodiment, the target molecule is a protein or peptide. For example, the target molecule is thrombin. The target molecules may be present in a solution, an extract or a formulation, which may be added to the oligomers at a concentration, ranged between 1 pM and 1 mM. The optimal concentration of the oligomers and the target molecule are chosen to minimize self-ligation of the oligomers or inter molecular ligation of the oligomers in the absence of a target molecule and to maximize the yield of ligated oligomers in the presence of target molecules. The target molecules and the oligomers are in contact in the mixture, which enable the oligomers to bind to the target molecules.

As noted, the oligomers refer to smaller fragments of oligonucleotides and may comprise 5 to 30 nucleotides. A set of short oligonucleotides are desirable for the present method. Suitable lengths of the oligomers may be in the range of 5 nucleotides to 10 nucleotides. In some embodiments, the length of the oligomers is 5 to 7 nucleotides. The oligonucleotides may include but are not limited to, 10 to 20 nucleotides, 15 to 30 nucleotides, 10 to 30 nucleotides, 10 to 25 nucleotides or combinations thereof. In this embodiment, the oligonucleotides are degenerate in all bases, have a 3' OH and adenylated at the 5' ends. In one embodiment, the oligomers containing 6 to 8 nucleotides with randomized sequence are used.

In the examples of method, the diversity of short oligomers is less, and may be represented at higher concentrations than in the case of SELEX. However, a balance of the concentration of oligomers with the target molecules is necessary to avoid non-templated ligation, wherein the "non-templated" ligation refers to ligation between short oligomers which are not bound to the target molecules. In some examples of the methods, the oligomers are dissolved in a buffer at a pH in a range of 5 to 8. In one example, the oligomers are dissolved in 10 mM HEPES buffer at pH 7.4. The concentration of dissolved oligomers is in a range, such as 1 fM to 10 nM.

The plurality of oligonucleotides have affinity for the target molecules. As noted, the method comprises forming an oligonucleotides-target molecule complex (or oligomers-target complex). The term "oligomers-target complex" refers to a complex wherein plurality of oligomers are bound to a target molecule. In one or more embodiments, the plurality of oligomers have affinity for the target molecules. The affinity of the oligomers for the target molecules may enhance the binding efficiency of the target molecules and the oligomers. In some embodiments, the oligonucleotides are bound to the target molecules by covalent interaction, ionic interaction, H-bonding, Vander Waal's forces or combinations thereof. In some embodiments, the oligomer-target complex is stabilized by adding a reaction buffer to the mixture. The stability of the complex is desired to complete ligation of the plurality of the oligomers present in the complex. The oligonucleotides may be modified to provide increased hydrophobicity.

The methods further comprise ligating the oligomers bound to each of the target molecules to form a binding-element. In one or more embodiments, the ligase present in the mixture initiates ligation of the ends of the short oligomers bound to each of the target molecules. The concurrent binding of oligomers to the target molecule in closer proximity facilitates the ligation reaction. For example, the oligomers bound to the target molecule in close proximity are ligated with a suitable ligase, such as CircLigase™. Two ligated oligomers may be expected to have increased affinity for the target molecule. The duration of binding and the concentration of the ligase may also affect, such as increase or decrease, the probability of ligating the oligomers present in close apposition.

The binding-elements may be synthesized by ligating the oligomers while they are transiently bound or associated with the target molecule. The transient binding of oligomers may allow the oligomers to be in close proximity for at least few seconds, which increases the probability of ligation of the ends of the oligomers bound to the target in the presence of a ligase. The transient binding of oligomers having affinity for the target molecule raises the effective local concentration of 3'-hydroxyl ends of oligomers and 5'-adenylated ends of oligomers. The increased concentration of 3'-hydroxyl and 5'-adenylated ends of oligomers results in efficient ligation of the 3'-hydroxyl ends and 5'-adenylated ends of two different target-bound oligomers. The kinetics of ligation reaction of the target-bound oligomers present in close proximity is analogous to a cyclization reaction of the single oligomer.

One or more ligases may be selected to ligate the ends of one or more of the short oligomers, such as a thermostable RNA ligase or T3 RNA ligase. For example, CircLigase™ may be used to ligate single stranded DNA into circles without the need for a template. The probability that the two ends of the oligomers are ligated is enhanced by the proximity of the two ends. In some embodiments, the ligation reaction of target-bound oligomers is concentration dependent. In some embodiments, CircLigase™ ligates two or more oligomers located in close proximity by virtue of being bound to a target molecule.

In one or more examples of the methods, CircLigase™, RNA ligase or T3 RNA ligase is added to the resultant mixtures of oligonucleotides and the target molecules, along with 1× reaction buffer followed by incubation. To achieve complete ligation in the presence of ligases and the reaction buffer, the optimum temperature may be maintained based on the optimal condition for the ligase used. This can be between 0° C. and 37° C. In one embodiment, the optimum temperature may be maintained at room temperature, in some other embodiments, the optimum temperature may be maintained at 30° C., or in some embodiments, the optimum temperature may be maintained at 20° C. In one embodiment, the mixtures are incubated for 1-5 hours at 20° C. In one embodiment, the ligation is achieved by incubating the mixture at 25° C. for 30 minutes.

The oligomers support a two-molecule ligation reaction in one conformation, and the oligomers in the specific conformation may neither be circularized alone or in combination. The oligomers are modified to prevent self-ligation (circularization) during the synthesis of binding-element. In some embodiments, the oligomers are dephosphorylated at 5' ends while the 3' OH ends remain intact and the dephosphorylation of the 5' ends prevents self-ligation of the oligomers. In some other embodiments, the oligomers are adenylated at the 5' ends and capped at the 3' ends with a 3' terminal blocking group to prevent self-ligation. In these embodiments, the blocking of the 3' ends may be achieved by using a phosphate or dideoxy nucleotide which is added onto a thioated penultimate base, or any other moiety that prevents the self-ligation. In one conformation, RNA ligase, T3 RNA ligase or thermostable RNA ligase, such as CircLigase™ may be used to ligate two oligomers without circularizing oligomers alone (self-ligation) or in combination (circularized with other oligomer). Linear single stranded DNA of greater than 30 bases is circularized by CircLigase™ enzyme, however, the reaction conditions are adjusted such that no linear concatemers or circular concatemers are produced. In various embodiments of the method, CircLigase™ ligates oligonucleotides bound to thrombin.

In one embodiment, the concentration of the oligomers and the target molecules may be selected so that the ligation of 3' OH ends with the 5' adenylated ends of two different oligomers is minimized in the absence of the target molecule. In another embodiment, an optimum concentration of oligomers, ligase and target molecules are selected to maximize the yield of ligated oligomers (or binding-elements) in presence of the target molecules. In combination, the concentrations of the oligomers, ligase and the target molecules are optimized for synthesis of binding-element to maximize the yield and minimize the self-ligation or non-template ligation of the oligomers.

The oligomers are selected for synthesizing binding-elements, wherein the binding-elements function as affinity ligands and are selected for high affinity binding to molecular targets. The binding-elements may comprise one or more binding moieties for the target molecules. A variety of binding-elements have been developed based on DNA and RNA, wherein the RNA binding-elements tend to be less stable than their DNA counterparts. DNA binding-elements are reliable for their pH and thermal stability, small size (~13 kDa) and potential for high binding capacity and therefore may be used as affinity binders for downstream processing, quantitation and characterization. In some embodiments, the binding-elements are ranging between 15-60 nucleotides in length.

As noted, the binding-elements are separated after synthesis. Prior to sequencing of the binding-elements, the purification of the reaction mixture after ligation may be necessary. In one or more embodiments, the method comprises separating the binding-elements from the impurities to further purify the binding-element pool before sequencing. In some embodiments, the binding-elements are separated from the target molecules, one or more un-ligated oligonucleotides, self-ligated oligonucleotides, non-template ligated oligonucleotides or other proteins or peptides. The impurities may comprise excess target molecules, excess un-ligated oligonucleotides, self-ligated linear or circular concatamers or non-template ligated oligonucleotides. The oligomers which are not bound to the target molecules may be referred to as "unbound" or "free" oligomers. The free oligomers may be present in the mixture after ligation as 'excess free oligomers'. In some embodiments, the impurities of ligated oligomers may comprise the oligomers which are ligated and the ligation is effected for free-oligomers. The free oligomers may be ligated to other free oligomers to form ligated oligomers, and may be referred to as "non-template ligated oligomers". In contrast, when the target-bound oligomers are ligated, those ligated oligomers lead to a binding-element. In some aspects, the lengths of the target-bound ligated oligomers are different. Selection of highly efficient binding-elements may be based on size of the binding-element, longer binding-elements may lead to greater target binding efficiency.

The binding-element may be separated from the impurities by one or more separation techniques. In some embodiments, the separation may be achieved based on the size of the ligated oligomers, self-ligated oligomers, un-ligated oligomers, target molecules or oligomer-target molecule complex. In some embodiments, the separation techniques may include chromatographic separation or electrophoretic separation. One or more embodiments of the chromatographic separation techniques comprise gel-filtration chromatography, ion-exchange chromatography, affinity chromatography or combinations thereof. In one embodiment, the chromatographic separation may include affinity chromatography. The affinity chromatography may further refine the binding-elements to remove any non-specifically bound excess oligomers, self-ligated linear or circularized concatamers or non-template ligated oligomers.

In some embodiments, following ligation, the mixtures are subjected to acid precipitation to precipitate proteins. The precipitated proteins may be separated from the supernatant by centrifugation. The precipitate is discarded and the supernatant is retained for further processing. For example, the post-ligation mixture is treated with trichloroacetic acid to precipitate proteins, followed by centrifugation. The manipulations that disrupt the secondary structure of the binding-element may lead to dissociation of the target molecule from the binding-element, enabling recovery of the target molecule using mild elution conditions. In some examples, a dissociation of the binding-element and the target molecule may be achieved by removal of divalent cations that stabilize the target-binding-element complex by use of a chelator. In some embodiments, the thrombin is used as a target and the binding-element specific to thrombin is dissociated by adding water to the thrombin-binding-element complex.

The supernatant is collected for downstream process and analysis. In some embodiments, the supernatant is subjected to chromatographic separation to isolate different fractions of oligomers, including ligated and un-ligated ones. For example, the supernatant is passed through an anion exchange HPLC column and fractions containing ligated-oligomers (binding-element) longer than the starting oligomers are collected. Ligated-oligomers or binding-elements are separated from the un-ligated fragments on the basis of size. The binding-elements are optionally further refined for affinity binding and subjected to sequencing.

In some embodiments, the resulting oligonucleotide mixture is treated to remove the blocking moiety at 3' end to form 3' de-protected and 5' phosphorylated oligonucleotides. In the case of a 3' dideoxy, the 3' terminal dideoxy nucleotide is removed by Exo I treatment, however the thiolated penultimate base prevents the degradation of the entire oligonucleotide by Exo I. In the case of a 3' phosphate, polynucleotide kinase is used both to remove the 3' phosphate and to phosphorylate the 5' end simultaneously. The de-blocking is effected to enable further manipulation of the oligonucleotide mixture for ligation of known sequences to the ends, or circularization.

In one or more embodiments, the method further comprises amplifying the binding-element to form an amplified binding-element sequence. The amplification comprises a polymerase chain reaction (PCR), an isothermal amplification, a rolling circle amplification or a multiple displacement amplification. In one embodiment, the amplification of oligonucleotides may be achieved by PCR amplification. Following PCR amplification, the mixture of the oligonucleotides and the target molecules is subjected to sequencing on a sequencing instrument. In some embodiments, the amplified binding-element sequence is configured to determine the target molecules from a sample comprising the target molecules. In these embodiments, the sample comprises target molecules and one or more molecules having similar structure as the target. The term "similar structure" may refer to the structure of the molecules having one or more structural motifs which are structurally identical or have partial similarity, wherein other motifs or domains of the molecules are different. In some embodiments, one or more adapter oligonucleotides are ligated to both the 3' and 5' ends of the elongated test oligonucleotides and are subjected to an amplification reaction.

The synthesized binding-elements may be sequenced using modern sequencing techniques followed by sequence analysis. The binding-element sequences may be analyzed to determine commonality of motifs in the sequences. The sequences of the ligated oligomers including the binding-elements are compared, wherein the sequences that contain oligonucleotide motifs with prevalence greater than ~1% are selected. In some examples, oligonucleotide sequences that have high motif prevalence are synthesized by chemical synthesis and designed to have a biotinylated poly T linker at one end of the oligonucleotide sequence. Each biotinylated oligonucleotide is then attached to a streptavidin chip and tested for affinity against the original target molecule.

The free-oligonucleotides (free-oligomers) recovered after separation of the binding-elements, are subjected to a binding assay in the presence of the target molecules to determine the dissociation constant ($K_d$) of the free-oligomers. The oligomers having dissociation constant, $K_d$' value less than 1 µM may be selected for further use. In some aspects, binding-elements with improved $K_d$ may be synthesized using various strategies. For example, the method may be modified to include a modified base in the short oligomer sets to modulate hydrophobicity of the oligomers. Oligonucleotides having the desired affinity may further be refined by synthesis of variants either by shortening the oligomers, deleting the bases, or substituting nucleotides to create binding motifs capable of specifically binding the target molecules.

The method of developing binding-elements in the presence of target molecules is schematically illustrated in FIG. 1. In one example, the short oligomers 22 and the target molecules 24 are provided as a mixture, as shown in step I. In step II, the oligomers 22 having affinity to target molecules, bind to each of the target molecules 24 to form oligomer-target complex 28. In some examples of the method, ligase 26 is added to the oligomer-target complex 28, as shown in step II. In some other examples, the ligase 26 may be added to the reaction mixture at the beginning, with the oligomers 22 and target molecule 24, wherein the oligomer-target complex 28 is formed in the presence of ligase 26. In step III, the oligomers bound to the target molecule are ligated to form ligated oligomers or binding-elements 30, when the ligated oligomers are attached to the target molecule 24. The ligation of oligomers is followed by separation and purification of binding-elements 30, as shown in step IV. Step IV comprises separation of binding-elements 30 from the un-ligated short oligomers 22 and target molecules 24 or other protein or peptide impurities. The purified binding-element 30 is further refined in step V, resulting in a refined, purified binding-element 32. The refined, purified binding-element is further subjected to sequence analysis in step VI. The binding-element sequences are characterized in step VII to form characterized binding-element 34, such as aptamers, which has sufficient affinity for the target molecules.

Figure 2:
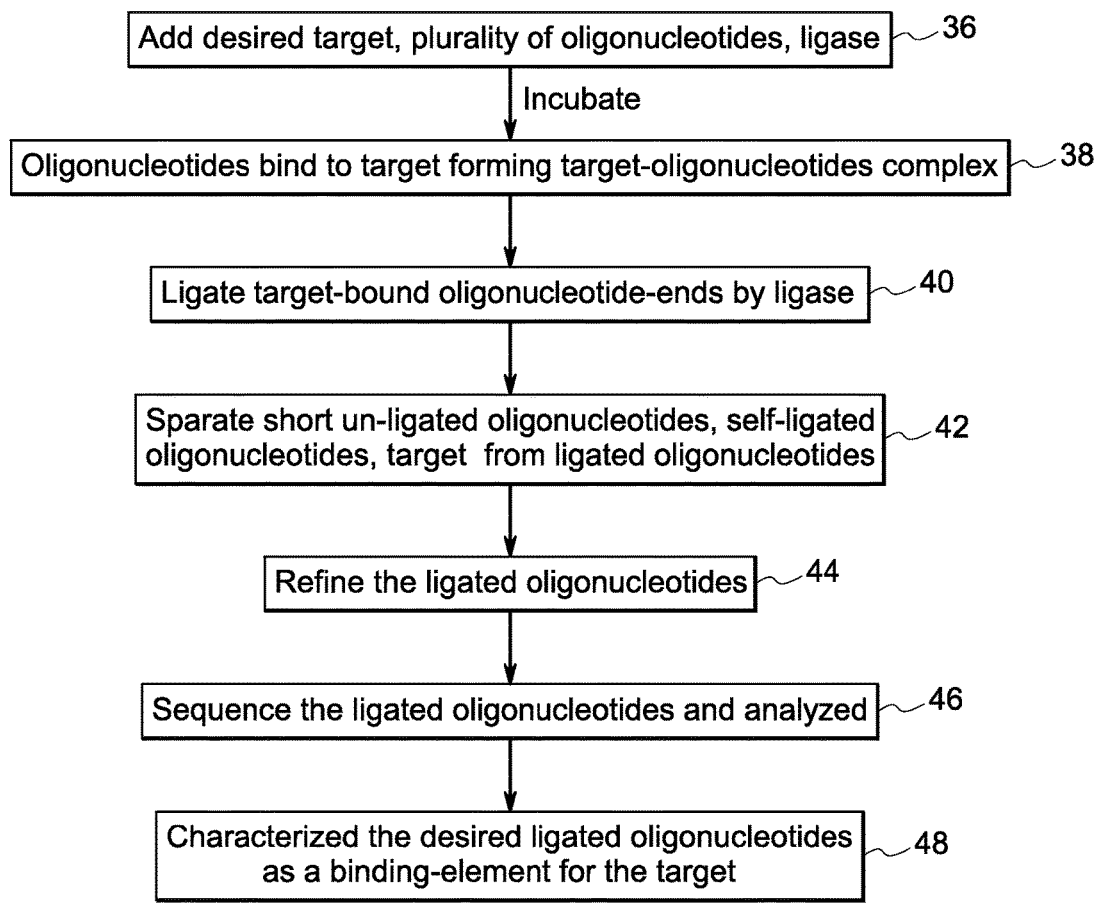
FIG. 2 is a flow chart showing method of synthesizing, selecting and purifying the binding-elements in accordance with one embodiment of the invention.

FIG. 2 is a flow chart illustrating an exemplary embodiment of a method for making and selecting a binding element for a specific target. In an alternative embodiment, some of the steps may be performed simultaneously or in different order. In some embodiments, one or more steps may be added to the flow chart. The flow chart of FIG. 2 includes the step 36 of adding short oligomers, desired target molecules and a ligase as a mixture. In step 38, the mixture of oligomers, target and ligase are incubated to initiate binding of the oligomers to the target molecule to form a target-oligomers complex. Step 40 comprises ligation of the target-bound oligomers by ligase to form a binding element. In some examples of the method, ligase is added to the oligomer-target complex during step 40. In some other examples, the ligase may be added to the reaction mixture at the beginning, with the oligomers and target molecule in step 36. In step 42, the binding-elements formed by ligation of the oligomers bound to the target molecule are separated and purified from the un-ligated short oligomers, self-ligated oligomers, target molecules or other protein or peptide impurities. In step 44, the purified binding elements are further refined. The refined, purified binding-element is further subjected to sequence analysis in step 46. The sequences of the binding-elements are characterized in step 48 to provide characterized binding-element, which has sufficient affinity for the target molecules.

Example 1. Synthesis and Selection of Binding-Elements Using Target Molecules

Reagents: DNA polymerase, Exonuclease I (Exo I) are stored in 50 mM Tris-HCl (pH 7.2), 200 mM NaCl, 10 mM DTT, 1 mM EDTA, 0.01% (v/v) Tween-20, and 50% (v/v) glycerol. CircLigase™ (NEB), RNA ligase or T3 RNA are dissolved in 10 mM HEPES buffer at pH 7.4 at a range of concentrations. The primer-nucleotide solution (primer-nucleotide mix) comprising primer and nucleotides (dNTPs) is used for PCR amplification.

Two sets of degenerate short oligomers containing 6 nucleotides with randomized sequence are used. In one set, the oligomers are dephosphorylated at 5' ends and have 3' OH ends to prevent self-ligation of the oligomers. In a second set, the oligomers are adenylated at the 5' ends and capped at the 3' ends with a 3' terminal blocking group to prevent self-ligation (with a phosphate or dideoxy nucleotide which has been added onto a thioated penultimate base that prevents ligation).

A protein, thrombin is used as the target molecule. Two different sets are prepared, wherein in one set, thrombin is added to the short oligomers at a concentration of 1 nM-20 μM. In the other set, oligomer alone is incubated under the same condition that facilitates complex formation, and both of the sets are subjected to ligation by CircLigase™. 1 pM-20 μM concentration of CircLigase™ is added to the resultant mixtures along with 1× reaction buffer that is devoid of rATP and the oligomer-thrombin-ligase mixture is incubated for 2 hours at 20° C. After ligation, the ligated products (binding-elements) are purified from thrombin.

Following incubation, the mixtures are treated with 100% trichloroacetic acid (1:5) to precipitate thrombin or any other proteins or peptides present in the mixture. The precipitate is separated by centrifugation and the supernatant is collected. The supernatant is further subjected to an anion exchange HPLC column (Mini Q-GE Healthcare) and fractions containing binding-elements (ligated-oligomers) longer than the starting oligonucleotides are collected.

The binding-elements between 12 and 24 nucleotides long are selected for cloning. The selected binding-elements are cloned and sequenced on the Ion Torrent Personal Genome Machine (PGM). Initially the sequences of the ligated oligomers including the binding-elements are compared and sequences that contain oligonucleotide motifs with prevalence greater than ~1% are selected. The selected binding-element sequences are subjected to PCR amplification using standard reagents and protocol.

Oligonucleotide sequences that have high motif prevalence are synthesized by standard chemical synthesis and designed to have a biotinylated poly T linker at one end of the oligonucleotide sequence. The sequences capable of binding to thrombin are identified using a binding assay and surface plasmon resonance technique. Each biotinylated oligonucleotide is then attached to a streptavidin chip (Biacore-GE Healthcare) and tested for affinity against the original target molecule using a Biacore 3000 instrument using the manufacturer's suggested protocol for determining binding efficiency.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A method for synthesizing a binding-element, comprising:
   providing a mixture comprising a plurality of target molecules, a plurality of oligonucleotides having randomized sequences and a ligase,
   forming an oligonucleotides-target molecule complex, wherein two or more of the oligonucleotides are bound to at least one of the target molecules;
   ligating the oligonucleotides bound to the at least one of the target molecules to form the binding-element, and
   separating the binding-element from one or more un-ligated or un-bound oligonucleotides of the plurality of oligonucleotides, wherein the binding element is configured to efficiently bind the at least one of the target molecules through one or more binding sites with higher affinity than the two or more oligonucleotides prior to the ligating.

2. The method of claim 1, wherein the target molecules comprise an organic molecule, an inorganic molecule, a synthetic molecule or combinations thereof.

3. The method of claim 1, wherein the target molecules comprise a protein, a peptide, a carbohydrate, a small molecule, a carrier, a drug or combinations thereof.

4. The method of claim 1, wherein the oligonucleotides comprise 4 to 60 nucleotides.

5. The method of claim 1, wherein the oligonucleotides comprise 4 to 10 nucleotides.

6. The method of claim 1, wherein the oligonucleotides are modified to provide increased hydrophobicity.

7. The method of claim 1, wherein the ligase comprises thermostable RNA ligase, T4 RNA ligase or combinations thereof.

8. The method of claim 1, wherein the oligonucleotides bind to the at least one of the target molecules by covalent interaction, ionic interaction, H-bonding, Vander Waal's forces or combinations thereof.

9. The method of claim 1, wherein the ligation is achieved by incubating the mixture between 0 to 37° C.

10. The method of claim 1, wherein the ligation is achieved by incubating the mixture at 25° C. for 30 minutes.

11. The method of claim 1, wherein the separating is achieved by acid-precipitation.

12. The method of claim 1, wherein the binding-element is separated from the one or more un-ligated oligonucleotides or un-bound oligonucleotides or combinations thereof by chromatographic techniques or electrophoretic techniques.

13. The method of claim 1, further comprising amplifying the binding-element to form an amplified binding-element sequence.

14. The method of claim 13, wherein the amplification comprises a polymerase chain reaction, isothermal amplification, rolling circle amplification or multiple displacement amplification.

15. The method of claim 13, further comprising sequencing the amplified binding-element sequence.

16. The method of claim 13, wherein the amplified binding-element sequence is configured to determine the target molecule from a sample comprising the target molecule.

17. The method of claim 1, wherein the binding-element comprises one or more tandem repeat sequences.

18. The method of claim 1, wherein the binding-element comprises a recombination site.

19. A method for synthesizing a binding-element, comprising:
   providing a mixture comprising a plurality of target molecules, a plurality of oligonucleotides having a plurality of sequences and a ligase,
   forming an oligonucleotides-target molecule complex comprising two or more oligonucleotides, wherein only a subset of the plurality of sequences are bound to at least one of the target molecules, wherein the at least one of the target molecules is a protein;
   ligating the oligonucleotides bound to the at least one of the target molecules to form the binding-element, and
   separating the binding-element from one or more un-ligated or un-bound oligonucleotides of the plurality of oligonucleotides, wherein the binding-element is configured to efficiently bind the at least one of the target molecules through one or more binding sites with higher affinity than the two or more oligonucleotides prior to the ligating.

20. The method of claim 19, wherein the oligonucleotides are single-stranded and wherein the ligating comprises ligating single-stranded ends of the two or more oligonucleotides to one another in a template-independent ligation.

21. A method for synthesizing a binding-element, comprising:
   providing a mixture comprising a plurality of target molecules, a plurality of single-stranded oligonucleotides having a plurality of sequences and a ligase,
   forming an oligonucleotides-target molecule complex, wherein only a subset of the plurality of sequences are bound to at least one of the target molecules;
   ligating single-stranded ends of the oligonucleotides bound to the at least one of the target molecules to one another to form the binding-element, wherein the ligating of the single-stranded ends to one another is in a template-independent manner, and
   separating the binding-element from one or more un-ligated or un-bound oligonucleotides of the plurality of oligonucleotides, wherein the binding-element is configured to efficiently bind the at least one of the target molecules through one or more binding sites.

22. The method of claim 1, wherein the oligonucleotides bind to different locations on the same target molecule.

23. The method of claim 22, wherein the target molecule is a protein.

24. The method of claim 1, wherein the oligonucleotides are dephosphorylated or adenylated at their 5' ends.

25. The method of claim 1, wherein the oligonucleotides are capped at their 3' ends.

* * * * *